United States Patent [19]
Croll

[11] Patent Number: 4,919,615
[45] Date of Patent: Apr. 24, 1990

[54] ORTHODONTIC BAND CAP

[76] Inventor: Theodore P. Croll, 4242 Mechanicsville Rd., Mechanicsville, Pa. 18934

[21] Appl. No.: 344,382

[22] Filed: Apr. 28, 1989

[51] Int. Cl.$^5$ ............................................... A61C 3/00
[52] U.S. Cl. .......................................... 433/3; 433/23; 433/229
[58] Field of Search .................. 433/2, 3, 23, 24, 141, 433/215, 229, 9

[56] References Cited

U.S. PATENT DOCUMENTS 3,797,116  3/1974  Meeks ..................................... 433/3
4,192,068  3/1980  Wolfson .................................. 433/3

*Primary Examiner*—Cary E. Stone
*Attorney, Agent, or Firm*—Gregory J. Gore

[57] ABSTRACT

A disposable cap for use by dentists for facilitating the cementation process of orthodontic banding. The cap includes a two-piece construction employing an adhesive base portion with a peel-off cover. The base element contains the surface adhesive only in a central area where the orthodontic band should make contact with the cap. The cap further includes a pair of tabs that extend from opposite sides which are not coated with adhesive to facilitate use by a practitioner wearing rubber gloves.

2 Claims, 2 Drawing Sheets

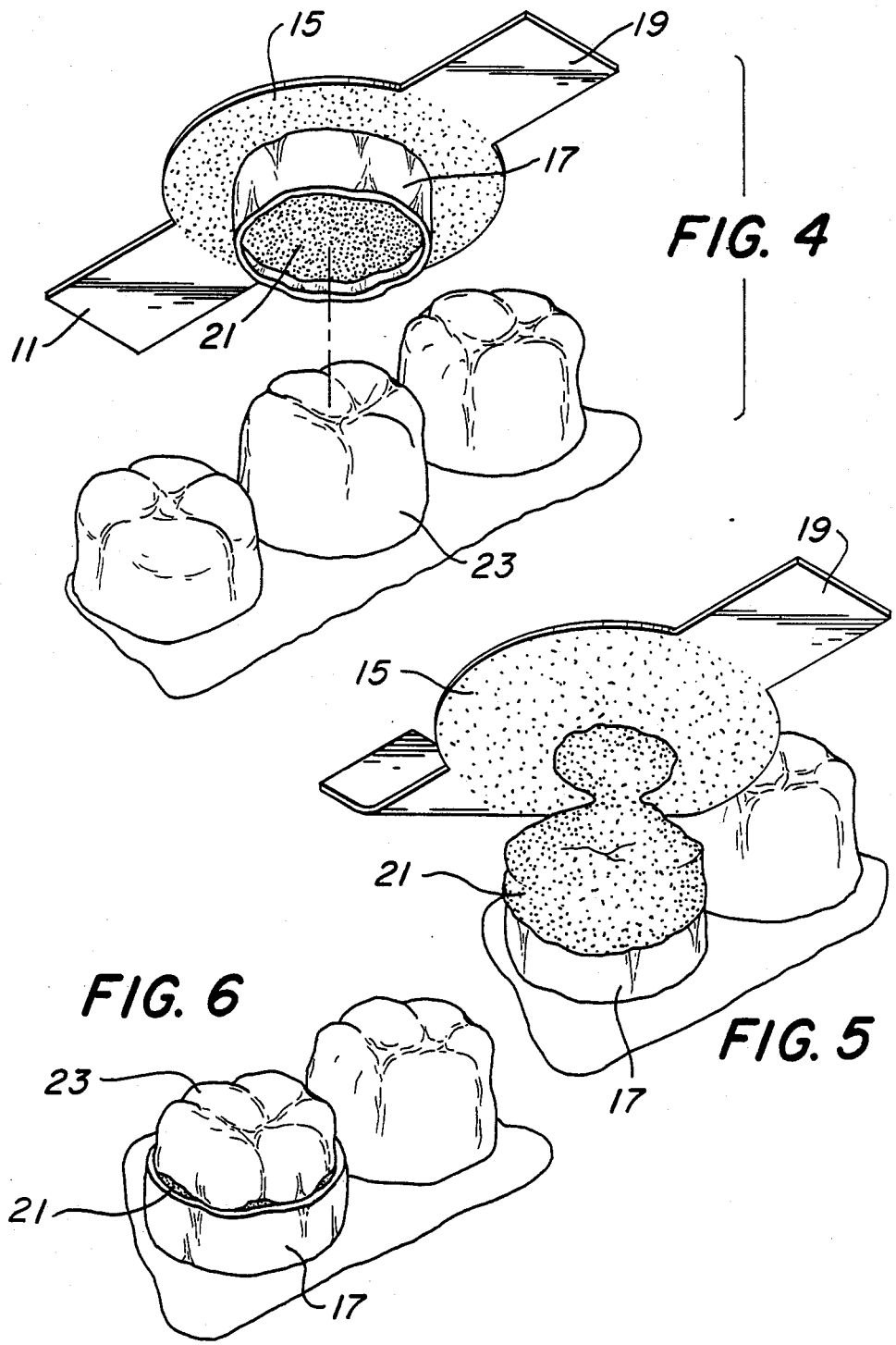

ORTHODONTIC BAND CAP

FIELD OF INVENTION

The present device relates to the process of applying metal bands around human teeth in the fields of orthodontics and general dentistry. More specifically, this device comprises a removable cap that is designed to be fitted over the top of the orthodontic band to facilitate cementation of the band to the tooth.

BACKGROUND OF THE INVENTION AND PRIOR ART

It is quite common in orthodontics and general dentistry to cement metal bands around teeth for a variety of purposes. Dentists routinely use cemented bands for space maintainers and all types of interceptive orthodontic devices.

A preferred means of carrying out metal band cementation was described by the applicant in the *Journal of Pedodontics*, Volume 7, Number 2, at page 120, entitled "Cementation of Stainless Steel Space Maintainers" (1983). The procedure described in this article explains the use of a small strip of autoclave masking tape pressed over the occlusal surface of the band in order to create a cup for filling the band with cement. The band, the tape, and cement are then positioned on the tooth and forced down over the tooth, the tape serving to force the cement gingivally and ensure that voids do not occur between the tooth and band due to occlusal escape of the cement.

BRIEF SUMMARY OF THE INVENTION

While this procedure which includes the use of masking tape is advantageous, it nonetheless has various drawbacks. First, the tape is incorrectly sized for this procedure and it is difficult to trim. Secondly, the use of rubber gloves makes the tape extremely difficult to handle because it sticks to the gloves with greater adhesion than it sticks to the orthodontic band. The present device solves these problems by providing a unique two-piece band cap which contains a surface adhesive only in the central area where the orthodontic band should make contact with the cap. The adhesive is covered by a removable strip until the cap is ready for use. The cap further includes a pair of tabs that extend from opposite sides which are not coated with adhesive.

BRIEF DESCRIPTION OF THE DRAWINGS

FIG. 4 shows the combination of FIG. 3 being inserted around a tooth.

FIG. 5 shows the band cap being removed from the orthodontic band and cement after it has been properly positioned around the tooth.

FIG. 6 shows the band properly cemented about the base of the tooth with all excess cement removed.

DESCRIPTION OF THE PREFERRED EMBODIMENT

Figure 1:
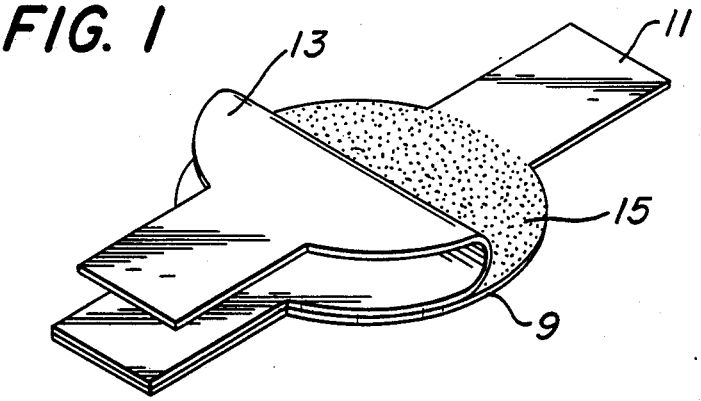
FIG. 1 is a top isometric view of the present device showing the two-layer construction and the cover layer partially peeled away.

Referring now to FIG. 1, the present cap is of simple, two-piece construction, each piece being composed of paper. The top layer 13 is a peel-off cover to isolate the adhesive 15 until it is ready for use. Surface adhesive 15 is applied to the top of a substantially circular central portion of the base element 9 which forms a cap when applied to an orthodontic band.

Figure 2:
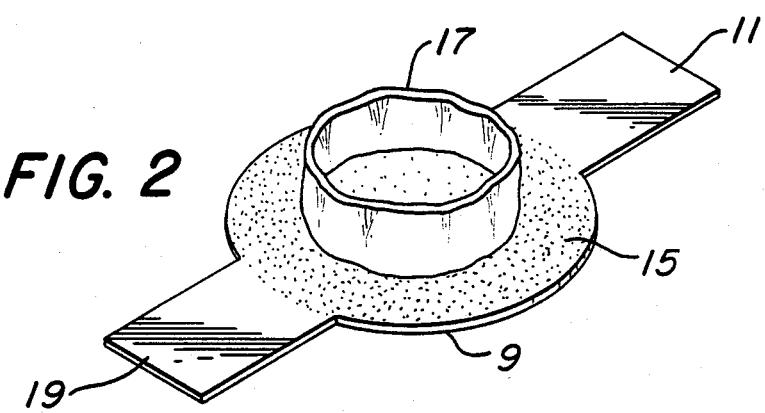
FIG. 2 is a top isometric view showing the orthodontic band placed properly in the center of the present device.

Referring now to FIG. 2, orthodontic band 17 is properly positioned in the center of adhesive portion 15. The base element 9 includes two opposing tabs 11 and 19 extending from opposite sides. Tabs 11 and 19 do not include any surface adhesive so that they may be conveniently handled by a practitioner wearing rubber gloves without touching any adhesive.

Figure 3:
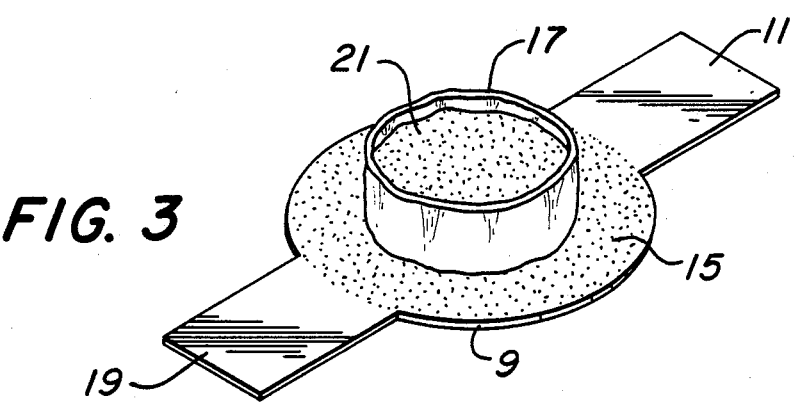
FIG. 3 shows the combination of FIG. 2, but with cement added to the cavity formed by the band and cap.

Referring now to FIG. 3, cement 21 is added in the cup formed by the orthodontic band and the adhesive cap. This cup acts as a means for both measuring and transporting the cement to the tooth. Next, as shown in FIG. 4, the capped orthodontic band carrying the cement is positioned over the tooth 23 to be banded, and pressed into place with the appropriate band-seating instrument. Then, as shown in FIG. 5, the adhesive cap is removed by pulling tab 19 away from the tooth. The next step, after initial cement hardening, is to remove excess cement yielding the orthodontic band properly cemented to tooth 23, as shown in FIG. 6.

Isolating the adhesive on the band cap from the user by providing a peel-off cover and non-adhesive tabs makes the procedure of using a band cap greatly enhanced and most often yields a superior result in less time.

It should be understood that the above description discloses specific embodiments of the present invention and are for purposes of illustration only. There may be other modifications and changes obvious to those of ordinary skill in the art which fall within the scope of the present invention which should be limited only the following claims and their legal equivalents.

What is claimed is:

1. In dentistry, a cap for an orthodontic band to facilitate cementation thereof, comprising:
   a. a thin, flat base element having a substantially circular central portion containing a surface adhesive;
   b. two or more tabs extending from the edge of said central portion, said tabs not containing any surface adhesive and being part of said base element; and,
   c. a peel-off cover at least co-extensive with said surface adhesive applied to the top surface of said central portion for isolating the adhesive until it is ready for use.

2. The orthodontic band cap of claim 1 wherein said cover and said base element are made of paper.

* * * * *